(12) United States Patent
Brunelle

(10) Patent No.: US 7,705,190 B2
(45) Date of Patent: Apr. 27, 2010

(54) METHOD OF MAKING AN AROMATIC POLYETHER COMPOSITION USING PHOSPHAZENIUM SALT PHASE TRANSFER CATALYSTS

(75) Inventor: Daniel Joseph Brunelle, Burnt Hills, NY (US)

(73) Assignee: Sabic Innovative Plastics IP B.V. (NL)

( * ) Notice: Subject to any disclaimer, the term of this patent is extended or adjusted under 35 U.S.C. 154(b) by 14 days.

(21) Appl. No.: 11/651,167

(22) Filed: Jan. 9, 2007

(65) Prior Publication Data

US 2007/0112223 A1 May 17, 2007

Related U.S. Application Data

(62) Division of application No. 10/950,874, filed on Sep. 24, 2004, now abandoned.

(51) Int. Cl.
*C07C 41/00* (2006.01)
(52) U.S. Cl. .................................. 568/660; 548/455
(58) Field of Classification Search ............... 568/660; 548/455
See application file for complete search history.

(56) References Cited

U.S. PATENT DOCUMENTS

| 2,991,273 | A | 7/1961 | Hechelhammer et al. |
| 2,999,835 | A | 9/1961 | Goldberg |
| 3,028,365 | A | 4/1962 | Schnell et al. |
| 3,148,172 | A | 9/1964 | Fox |
| 3,153,008 | A | 10/1964 | Fox |
| 3,271,367 | A | 9/1966 | Schnell et al. |
| 3,271,368 | A | 9/1966 | Goldberg et al. |
| 4,217,438 | A | 8/1980 | Brunelle et al. |
| 4,273,712 | A | 6/1981 | Williams, III |
| 4,362,857 | A | 12/1982 | Yonezawa |
| 4,460,778 | A | 7/1984 | Brunelle |
| 4,513,141 | A | 4/1985 | Brunelle et al. |
| 4,554,357 | A | 11/1985 | Verbicky, Jr. et al. |
| 4,681,949 | A | 7/1987 | Brunelle |
| 5,081,298 | A | 1/1992 | Brunelle |
| 5,116,975 | A | 5/1992 | Brunelle |
| 5,132,423 | A | 7/1992 | Brunelle et al. |
| 5,990,352 | A | 11/1999 | Nobori et al. |
| 6,130,346 | A | * 10/2000 | Nobori et al. .................. 558/51 |
| 6,184,425 | B1 | 2/2001 | Kolomeitsev et al. |
| 6,465,643 | B1 | 10/2002 | Schiemenz et al. |
| 6,469,224 | B1 | * 10/2002 | Nobori et al. ................ 585/400 |
| 6,489,218 | B1 | * 12/2002 | Kim et al. ..................... 438/460 |
| 6,528,599 | B1 | 3/2003 | Nobori et al. |
| 2002/0161227 | A1 | * 10/2002 | Nobori et al. ................ 544/337 |
| 2006/0241300 | A1 | 10/2006 | Wessel et al. |

FOREIGN PATENT DOCUMENTS

| JP | 61014262 | * | 1/1986 |
| WO | 9422939 A | | 10/1994 |

OTHER PUBLICATIONS

Schwesinger, et al., "Peralkylated Polyaminophosphazenes—Extremely Strong, Neutral Nitrogen Bases", Angewandte Chemie International Edition in English, vol. 26, No. 11, 1987, pp. 1167-1169, XP002536763.
Dehmlow E V, et al., "Notiz Uber Die Steuerung Von 0-/C-Alkylierungen Mit Hilfe Von Phasentransfer-Katalysatoren/ /Directing Effects on O- vs. C-Alkylations by Phase Transfer Catalysts", Chemische Berichte, Verlag Chemie GmbH, Weinheim, DE, vol. 126, No. 12, Jan. 1, 1993, pp. 2765-2766, XP001084482.
Pleschke A, et al., Halex reactions of aromatic compounds catalysed by 2-azaallenium, carbophosphazenium, aminophosphonium and diphosphazenium salts: a comparative study, Journal of Flourine Chemistry, Elsevier, NL, vol. 125, No. 6, Jun. 1, 2004, pp. 1031-1038, XP004586028.
Hoffman U, et al., "Phase-Transfer Catalyzed Synthesis of Poly(etherketone)s", Polymer Bulletin, Springer, Heidelberg, DE, vol. 30, No. 5, May 1, 1993, pp. 481-488, XP000372809.
DE10232811, published Dec. 24, 2003, Abstract Only, 1 page.
European Search Report for Application No. 05255859.0, mailed Jul. 23, 2009, 11 pages.

* cited by examiner

*Primary Examiner*—Sikarl A Witherspoon
*Assistant Examiner*—Chukwuma O Nwaonicha
(74) *Attorney, Agent, or Firm*—Cantor Colburn LLP

(57) ABSTRACT

A method for carrying out a chemical reaction between at least two reactants occupying separate phases within a multiphase reaction mixture has been discovered in which at least one phosphazenium salt is employed as a phase transfer catalyst. The remarkable utility of phosphazenium salts as phase transfer catalysts is illustrated by the preparation of aromatic ethers. The phosphazenium salt phase transfer catalysts are shown to be especially useful in the preparation of aromatic polyethers such as polyether sulfones.

1 Claim, 4 Drawing Sheets

METHOD OF MAKING AN AROMATIC POLYETHER COMPOSITION USING PHOSPHAZENIUM SALT PHASE TRANSFER CATALYSTS

BACKGROUND OF THE INVENTION

This invention relates to use of phosphazenium salts as phase transfer catalysts. In one aspect the invention relates to a method of making aromatic ethers. More particularly, the method relates to a method of preparing aromatic ethers using exceptionally stable phosphazenium salt phase transfer catalysts.

Various types of aromatic ethers have gained prominence due to their utility in diverse fields as agricultural chemistry, medicinal chemistry and polymer chemistry. One class of aromatic ethers, aromatic polyethers (e.g. See for example polyethersulfones, polyetherimides, and polyetherketones), are important engineering resins due to their exceptional chemical and physical properties.

Aromatic ethers are typically prepared by synthetic methodology involving the reaction of the salt of an aromatic hydroxy compound with an aromatic compound comprising at least one suitable leaving group. In one general methodology, aromatic ethers are prepared in a nucleophilic aromatic substitution reaction between a nucelophilic aromatic hydroxy compound and an electrophonic aromatic compound comprising at least one suitable leaving group, the reaction being mediated by a stoichiometric amount of a basic reactant such as an alkali metal hydroxide or alkali metal carbonate. Typically, such nucleophilic aromatic substitution reactions must be carried out in polar aprotic solvents such as dimethylformamide, dimethylacetamide, N-methylpyrrolidinone, dimethyl sulfoxide, or sulfolane in order to achieve synthetically useful rates of conversion of starting materials to product aromatic ethers. In such cases, drying, recovery, and reuse of the solvent is cumbersome and expensive.

Various phase transfer catalysts (PTC's) are known to accelerate reaction rates of chemical reactions generally. Phase transfer catalysts are typically most effective when the chemical reaction involves reactants which tend to segregate into separate phases. Among other benefits, the use of phase transfer catalysts is known to enable the use of solvents in which one or more of the reactants is insoluble in the absence of the phase transfer catalyst.

Known phase transfer catalysts include quaternary ammonium salts, quaternary phosphonium salts, and hexaalkylguanidinium salts. Of the known phase transfer catalysts, quaternary ammonium salts are stable at ambient temperature, but decompose rapidly at temperatures in excess of about 100° C. Quaternary phosphonium salts are more stable, but their use typically results in a lower reaction rate relative to the reaction rate observed in the corresponding reaction in which a quaternary ammonium salt phase transfer catalyst is employed. Thus, higher levels of phosphonium salt phase transfer catalyst must be used in order to achieve reaction rates comparable to reaction rates attained using quaternary ammonium salt phase transfer catalysts. Hexaalkylguanidinium salts are effective phase transfer catalysts but nonetheless are subject to decomposition at higher temperatures.

Much attention has been directed in recent years to organic reactions in heterogeneous systems, employing a phase transfer catalyst which facilitates the migration of a reactant into a phase from which it is normally absent. Many types of phase transfer catalysts are known to be effective under such conditions, including quaternary ammonium and phosphonium salts as disclosed in U.S. Pat. No. 4,273,712. Additionally, various bis-quaternary ammonium or phosphonium salts have been used as disclosed in U.S. Pat. No. 4,554,357; and aminopyridinium salts have been used as disclosed in U.S. Pat. Nos. 4,460,778, 4,513,141 and 4,681,949. Hexaalkylguanidinium salts, and their bis-salt analogues have been used as phase transfer catalysts as disclosed in U.S. Pat. Nos. 5,132,423; 5,116,975; and 5,081,298.

Nucleophilic aromatic substitution reactions, also referred to as "nucleophilic aromatic displacement reactions" often require heating a highly insoluble salt of an aromatic hydroxy compound with a soluble aromatic compound comprising at least one suitable leaving group in a relatively nonpolar solvent such as o-dichlorobenzene (o-DCB) in the presence of a phase transfer catalyst. Frequently, for synthetically useful reaction rates to be achieved, the reaction mixture must be heated to a temperature at which the phase transfer catalyst decomposes. While a prodigious technical effort has been expended in the development of more thermally stable phase transfer catalysts (See for example the development of 4-dialkylaminopyridinium salt catalysts and hexaalkylguanidinium salt catalysts), improved phase transfer catalyst thermal stability remains an important objective.

It would be highly desirable, therefore, to discover phase transfer catalysts having improved stability that could be used under a wide variety of reaction conditions, including the formation of aromatic ethers.

BRIEF SUMMARY OF THE INVENTION

In one aspect the present invention provides phosphazenium salts and their use as phase transfer catalysts generally.

In another aspect the present invention provides a method for making aromatic ethers comprising contacting in a reaction mixture the salt of at least one aromatic hydroxy compound with at least one aromatic compound comprising at least one leaving group, said contacting being carried out in the presence of a phosphazenium salt having structure I

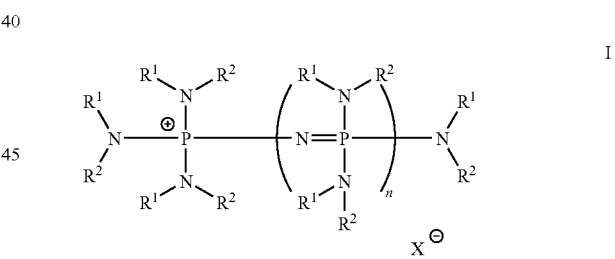

wherein n is an integer from zero to about 10, $R^1$ and $R^2$ are independently selected from the group consisting of $C_1$-$C_{20}$ aliphatic radicals, $C_3$-$C_{20}$ cycloaliphatic radicals, and $C_4$-$C_{20}$ aromatic radicals, and wherein said $R^1$ and $R^2$ may be linked together form a cyclic structure comprising at least one nitrogen atom, and wherein $X^-$ is selected from the group consisting of monovalent inorganic anions, monovalent organic anions, polyvalent inorganic anions, polyvalent organic anions, and mixtures thereof.

In another aspect the present invention provides a method for making aromatic polyether compositions, said method comprising contacting in a reaction mixture the salt of at least one aromatic dihydroxy compound with at least one aromatic compound bearing at least two leaving groups, said contacting being carried out in the presence of a phosphazenium salt having structure I.

DETAILED DESCRIPTION OF THE INVENTION

Figure 1:
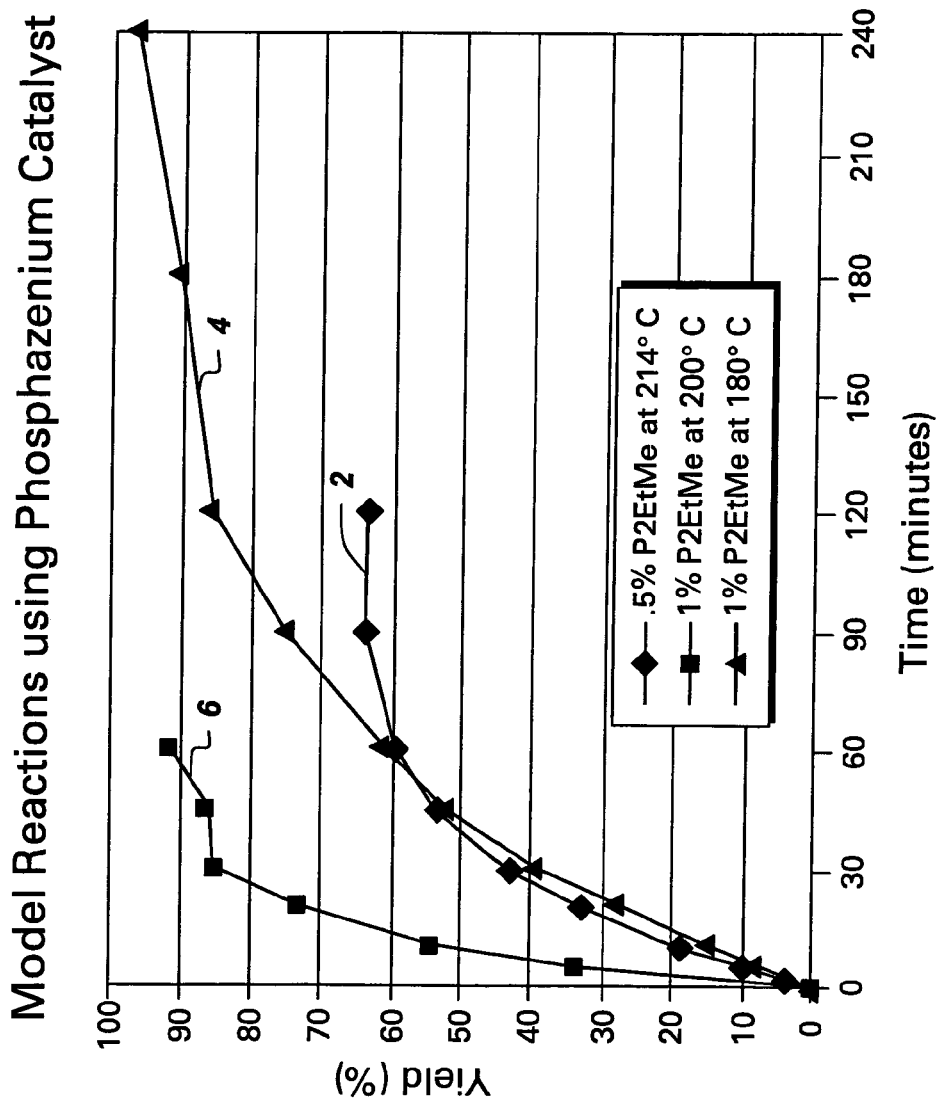
FIG. 1 illustrates the reaction kinetics observed in a series of reactions involving the 4-chlorophenyl phenyl sulfone and the disodium salt of bisphenol A in the presence of a phosphazenium salt phase transfer catalyst at various temperatures.

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein the term "BPA" refers to bisphenol A.

As used herein the term "aliphatic radical" refers to a radical having a valence of at least one comprising a linear or branched array of atoms which is not cyclic. The array may include heteroatoms such as nitrogen, sulfur, silicon, selenium and oxygen or may be composed exclusively of carbon and hydrogen. Aliphatic radicals may be "substituted" or "unsubstituted". A substituted aliphatic radical is defined as an aliphatic radical which comprises at least one substituent. A substituted aliphatic radical may comprise as many substituents as there are positions available on the aliphatic radical for substitution. Substituents which may be present on an aliphatic radical include but are not limited to halogen atoms such as fluorine, chlorine, bromine, and iodine. Substituted aliphatic radicals include trifluoromethyl, hexafluoroisopropylidene, chloromethyl; difluorovinylidene; trichloromethyl, bromoethyl, bromotrimethylene (e.g. —CH$_2$CHBrCH$_2$—), and the like. For convenience, the term "unsubstituted aliphatic radical" is defined herein to encompass, as part of the "linear or branched array of atoms which is not cyclic" comprising the unsubstituted aliphatic radical, a wide range of functional groups. Examples of unsubstituted aliphatic radicals include allyl, aminocarbonyl (i.e. —CONH$_2$), carbonyl, dicyanoisopropylidene (i.e. —CH$_2$C(CN)$_2$CH$_2$—), methyl (i.e. —CH$_3$), methylene (i.e. —CH$_2$—), ethyl, ethylene, formyl, hexyl, hexamethylene, hydroxymethyl (i.e. —CH$_2$OH), mercaptomethyl (i.e. —CH$_2$SH), methylthio (i.e. —SCH$_3$), methylthiomethyl (i.e. —CH$_2$SCH$_3$), methoxy, methoxycarbonyl, nitromethyl (i.e. —CH$_2$NO$_2$), thiocarbonyl, trimethylsilyl, t-butyldimethylsilyl, trimethyoxysilypropyl, vinyl, vinylidene, and the like. Aliphatic radicals are defined to comprise at least one carbon atom. A C$_1$-C$_{10}$ aliphatic radical includes substituted aliphatic radicals and unsubstituted aliphatic radicals containing at least one but no more than 10 carbon atoms.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group (C$_6$H$_3$) fused to a nonaromatic component —(CH$_2$)$_4$—. Aromatic radicals may be "substituted" or "unsubstituted". A substituted aromatic radical is defined as an aromatic radical which comprises at least one substituent. A substituted aromatic radical may comprise as many substituents as there are positions available on the aromatic radical for substitution. Substituents which may be present on an aromatic radical include, but are not limited to halogen atoms such as fluorine, chlorine, bromine, and iodine. Substituted aromatic radicals include trifluoromethylphenyl, hexafluoroisopropylidenebis(4-phenyloxy) (i.e. —OPhC(CF$_3$)$_2$PhO—), chloromethylphenyl; 3-trifluorovinyl-2-thienyl; 3-trichloromethylphenyl (i.e. 3-CCl$_3$Ph—), bromopropylphenyl (i.e. BrCH$_2$CH$_2$CH$_2$Ph—), and the like. For convenience, the term "unsubstituted aromatic radical" is defined herein to encompass, as part of the "array of atoms having a valence of at least one comprising at least one aromatic group", a wide range of functional groups. Examples of unsubstituted aromatic radicals include 4-allyloxyphenoxy, aminophenyl (i.e. H$_2$NPh—), aminocarbonylphenyl (i.e. NH$_2$COPh—), 4-benzoylphenyl, dicyanoisopropylidenebis (4-phenyloxy) (i.e. —OPhC(CN)$_2$PhO—), 3-methylphenyl, methylenebis(4-phenyloxy) (i.e. —OPhCH$_2$PhO—), ethylphenyl, phenylethenyl, 3-formyl-2-thienyl, 2-hexyl-5-furanyl; hexamethylene-1,6-bis(4-phenyloxy) (i.e. —OPh(CH$_2$)$_6$PhO—); 4-hydroxymethylphenyl (i.e. 4-HOCH$_2$Ph—), 4-mercaptomethylphemyl (i.e. 4-HSCH$_2$Ph—), 4-methylthiophenyl (i.e. 4-CH$_3$SPh—), methoxyphenyl, methoxycarbonylphenyloxy (e.g. methyl salicyl), nitromethylphenyl (i.e. —PhCH$_2$NO$_2$), trimethylsilylphenyl, t-butyldimethylsilylphenyl, vinylphenyl, vinylidenebis(phenyl), and the like. The term "a C$_3$-C$_{10}$ aromatic radical" includes substituted aromatic radicals and unsubstituted aromatic radicals containing at least three but no more than 10 carbon atoms. The aromatic radical 1-imidazolyl (C$_3$H$_2$N$_2$—) represents a C$_3$ aromatic radical. The benzyl radical (C$_7$H$_8$—) represents a C$_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethy group (C$_6$H$_{11}$CH$_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. Cycloaliphatic radicals may be "substituted" or "unsubstituted". A substituted cycloaliphatic radical is defined as a cycloaliphatic radical which comprises at least one substituent. A substituted cycloaliphatic radical may comprise as many substituents as there are positions available on the cycloaliphatic radical for substitution. Substituents which may be present on a cycloaliphatic radical include but are not limited to halogen atoms such as fluorine, chlorine, bromine, and iodine. Substituted cycloaliphatic radicals include trifluoromethylcyclohexyl, hexafluoroisopropylidenebis(4-cyclohexyloxy) (i.e. —OC$_6$H$_{11}$C(CF$_3$)$_2$ C$_6$H$_{11}$O—), chloromethylcyclohexyl; 3-trifluorovinyl-2-cyclopropyl; 3-trichloromethylcyclohexyl (i.e. 3-CCl$_3$C$_6$H$_{11}$—), bromopropylcyclohexyl (i.e. BrCH$_2$CH$_2$CH$_2$C$_6$H$_{11}$—), and the like. For convenience, the term "unsubstituted cycloaliphatic radical" is defined herein to encompass a wide range of functional groups. Examples of unsubstituted cycloaliphatic radicals include 4-allyloxycyclohexyl, aminocyclohexyl (i.e. H$_2$N C$_6$H$_{11}$—), aminocarbonylcyclopenyl (i.e. NH$_2$COC$_5$H$_9$—), 4-acetyloxycyclohexyl, dicyanoisopropylidenebis(4-cyclohexyloxy) (i.e. —OC$_6$H$_{11}$C(CN)$_2$C$_6$H$_{11}$O—), 3-methylcyclohexyl, methylenebis(4-cyclohexyloxy) (i.e. —OC$_6$H$_{11}$CH$_2$C$_6$H$_{11}$O—), ethylcyclobutyl, cyclopropylethenyl, 3-formyl-2-terahydrofuranyl, 2-hexyl-5-tetrahydrofuranyl; hexamethylene-1,6-bis (4-cyclohexyloxy) (i.e. —OC$_6$H$_{11}$(CH$_2$)$_6$C$_6$H$_{11}$O—); 4-hydroxymethylcyclohexyl (i.e. 4-HOCH$_2$C$_6$H$_{11}$—), 4-mercaptomethylcyclohexyl (i.e. 4-HSCH$_2$C$_6$H$_{11}$—), 4-methylthiocyclohexyl (i.e. 4-CH$_3$SC$_6$H$_{11}$—), 4-methoxycyclohexyl, 2-methoxycarbonylcyclohexyloxy (2-CH$_3$OCO C$_6$H$_{11}$O—), nitromethylcyclohexyl (i.e. NO$_2$CH$_2$C$_6$H$_{10}$—), trimethylsilylcyclohexyl, t-butyldimethylsilylcyclopentyl, 4-trimethoxysilyethylcyclohexyl (e.g. (CH$_3$O)$_3$SiCH$_2$CH$_2$C$_6$H$_{10}$—), vinylcyclohexenyl, vinylidenebis(cyclohexyl), and the like. The term "a C$_3$-C$_{10}$ cycloaliphatic radical" includes substituted cycloaliphatic radicals and unsubstituted cycloaliphatic radicals containing at least three but no more than 10 carbon atoms. The cycloaliphatic radical 2-tetrahydrofuranyl (C$_4$H$_7$O—) represents a C$_4$ cycloaliphatic radical. The cyclohexylmethyl radical (C$_6$H$_{11}$CH$_2$—) represents a C$_7$ cycloaliphatic radical.

As noted, the present invention provides phosphazenium salts and their use as phase transfer catalysts generally. Thus, it has been discovered that phosphazenium salts make outstanding phase transfer catalysts, in part due to the very high level of thermal stability phosphazenium salts exhibit. In one embodiment, the present invention provides a method for carrying out a chemical reaction between at least two reactants occupying separate phases within a multiphase reaction mixture comprising at least one phosphazenium salt phase transfer catalyst. Although, the utility of phosphazenium salts as phase transfer catalysts is illustrated experimentally herein in terms of multiphase reactions involving the formation aryl ethers, the present invention encompasses the use generally of phosphazenium salts as phase transfer catalysts in multiphase reactions. Thus, in the description and experimental details which follow, the use of phosphazenium salts as phase transfer catalysts is illustrated by chemistry related to the formation of aromatic ethers but is in no way limited thereto. The scope of the present invention is not limited methods related to the formation of aryl ethers. In its broadest sense, the present invention includes the use of a phosphazenium salt in any and all multiphase reaction mixtures in which the phosphazenium salt functions as a phase transfer catalyst.

As noted, in one aspect the present invention relates to a method for making aromatic ethers. More particularly, the present invention relates to preparation of the aromatic ethers by contacting in a multiphase reaction mixture the salt of at least one aromatic hydroxy compound with at least one aromatic compound comprising at least one leaving group, said reaction mixture comprising a phosphazenium salt phase transfer catalyst.

In one embodiment, the phosphazenium salt has structure I

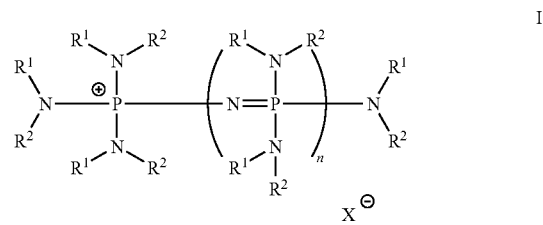

wherein n is an integer from zero to about 10, $R^1$ and $R^2$ are independently selected from the group consisting of $C_1$-$C_{20}$ aliphatic radicals, $C_3$-$C_{20}$ cycloaliphatic radicals, and $C_4$-$C_{20}$ aromatic radicals, and wherein said $R^1$ and $R^2$ may be linked together form a cyclic structure comprising at least one nitrogen atom, and wherein $X^-$ is selected from the group consisting of monovalent inorganic anions, monovalent organic anions, polyvalent inorganic anions, polyvalent organic anions, and mixtures thereof.

The positive charge in the cation shown in structure I is represented in a canonical form in which the positive charge is localized on a phosphorous atom. Those skilled in the art will understand that numerous canonical forms other than that featured in structure I are possible, and that the positive charge is considered to be delocalized over the whole molecule.

In one embodiment, $R^1$ and $R^2$ in the phosphazenium salt represented by the structure I are the same or different and each represents a hydrocarbon group having 1 to 10 carbon atoms, wherein $R^1$ and $R^2$ are at any occurrence independently selected from the group consisting of aliphatic and aromatic hydrocarbon groups. For example, $R^1$ and $R^2$ may be methyl, ethyl, n-propyl, isopropyl, allyl, n-butyl, sec-butyl, tert-butyl, 2-butenyl, 1-pentyl, 2-pentyl, 3-pentyl, 2-methyl-1-butyl, isopentyl, tert-pentyl, 3-methyl-2-butyl, neopentyl, n-hexyl, 4-methyl-2-pentyl, cyclopentyl, cyclohexyl, 1-heptyl, 3-heptyl, 1-octyl, 2-octyl, 2-ethyl-1-hexyl, 1,1-dimethyl-3,3-dimethylbutyl (popular name: tert-octyl), nonyl, decyl, phenyl, 4-toluyl, benzyl, 1-phenylethyl, and 2-phenylethyl. In one embodiment, $R^1$ and $R^2$ are aliphatic hydrocarbon groups having from 1 to 8 carbon atoms, such as methyl, ethyl, n-propyl, isopropyl, tert-butyl, tert-pentyl and 1,1-dimethyl-3,3-dimethylbutyl.

In an alternate embodiment $R^1$ and $R^2$ together form a cyclic structure comprising at least one nitrogen atom. In the case wherein both $R^1$ and $R^2$ are bound to the same nitrogen atom and both $R^1$ and $R^2$ represent aliphatic radicals, $R^1$ and $R^2$ may together form a cyclic structure comprising at least one nitrogen atom. Cyclic structures comprising one or more nitrogen atoms are exemplified by the pyrrolidin-1-yl group, the piperidin-1-yl group, the morpholin-4-yl group, and variants of those groups substituted by alkyl groups, for example methyl groups and ethyl groups.

In one embodiment the phosphazenium salt is selected from the group consisting of phosphazinum salts having structures II, III, IV, and V

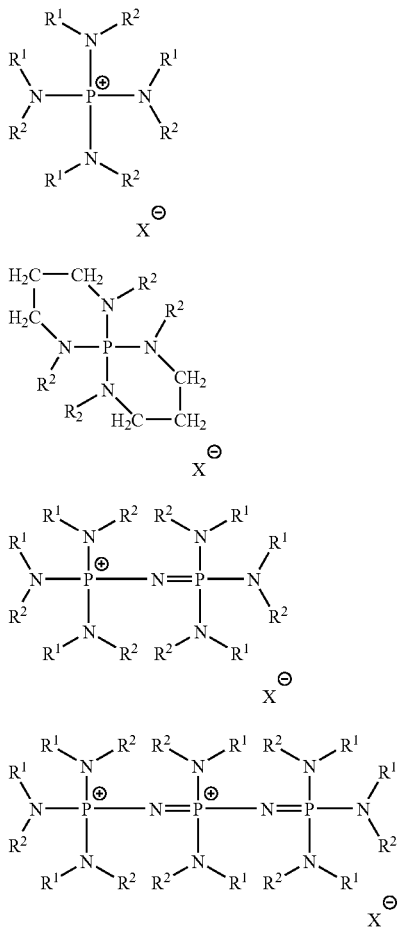

wherein $R^1$, $R^2$ and $X^-$ are defined as in structure I.

The anionic species $X^-$ shown in structures I-V is selected from the group consisting of monovalent inorganic anions, monovalent organic anions, polyvalent inorganic anions, polyvalent organic anions, and mixtures thereof. Monovalent inorganic anions include chloride, bromide, fluoride, methanesulfonate, hydrogensulfate, bicarbonate, and the like. Polyvalent inorganic anions include carbonate, sulfate, sulfite, and the like. Monovalent organic anions include methanesulfonate, acetate, alkoxide, acetylacetonate, and the like. Polyvalent organic anions include malonate, succinate, ethylenedisufonate (i.e. —O$_3$SCH$_2$CH$_2$SO$_3$—), and the like.

In one embodiment of the present invention, the salt of at least one aromatic hydroxy compound is contacted with at least one aromatic compound comprising at least one leaving group, said contacting being carried out in the presence of an effective amount of a phosphazenium salt having structure I. An effective amount of phosphazenium salt catalyst is defined as that amount of phosphazenium salt required to affect materially the outcome of the reaction. Typically, an effective amount of phosphazenium salt catalyst means an amount of phosphazenium salt needed to produce a measurable increase in a reaction rate, relative to the rate of reaction observed in the absence phosphazenium salt. In one embodiment, the phosphazenium salt is used in an amount corresponding to between about 0.1 and about 10 mole percent based upon the amount of the aromatic hydroxyl compound employed. In another embodiment, the phosphazenium salt is used in an amount corresponding to between about 0.2 and about 5 mole percent based upon the amount of the aromatic hydroxyl compound employed. In yet another embodiment, the phosphazenium salt is used in an amount corresponding to between about 0.5 and about 2 mole percent based upon the amount of the aromatic hydroxyl compound employed.

In one embodiment the salt of at least one aromatic hydroxy compound has structure VI

wherein $R^3$ is a $C_5$-$C_{40}$ aromatic radical; M is a metal selected from the group consisting of alkali metals, alkaline earth metals, and mixtures thereof; Z is oxygen, sulfur, or selenium, at least one Z being oxygen; and k is 1, 2 or 3.

Typically, the salt of at least one aromatic hydroxy compound is derived from the corresponding hydroxy compound by deprotonation. In one embodiment the at least one aromatic hydroxy compound is a dihydroxy aromatic compound of the formula VII

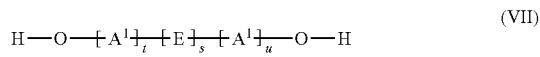

wherein $A^1$ is independently at each occurrence a $C_3$-$C_{20}$ aromatic radical; E is independently at each occurrence a bond, a $C_1$-$C_{20}$ aliphatic radical, a $C_3$-$C_{20}$ cycloaliphatic radical, or a $C_5$-$C_{20}$ aromatic radical, a sulfur atom, a sulfinyl group, a sulfonyl group, a selenium atom, or an oxygen atom; and t, s and u are independently integers from 0-10 wherein at least one of t, s and u is not zero.

Suitable aromatic radicals "$A^1$" include, but are not limited to, phenylene, biphenylene, naphthylene, and the like. Suitable groups "E" include but are not limited to alkylene and alkylidene groups, for example methylene, ethylene, ethylidene, propylene, propylidene, isopropylidene, butylene, butylidene, isobutylidene, amylene, amylidene, isoamylidene, and the like. The group "E" includes $C_5$-$C_{20}$ aromatic radicals for example the $C_{12}$ divalent aromatic radical represented by structure VIII, the dashed lines (Structure VIII) indicating the points of attachment of the radical to the $A^1$ groups shown in structure VII.

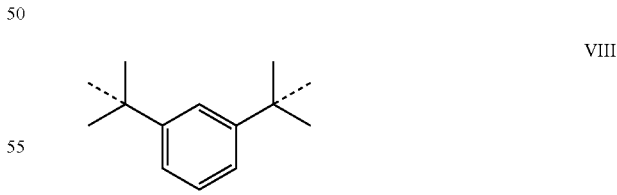

The group "E" may also be a tertiary nitrogen linkage; an ether linkage; a carbonyl linkage; a silicon-containing linkage, silane, siloxy; or a sulfur-containing linkage including, but not limited to, sulfide, sulfoxide, sulfone, and the like; or a phosphorus-containing linkage including, but not limited to, phosphinyl, phosphonyl, and the like. In other embodiments E may be a cycloaliphatic group including, but not limited to, 1,1-cyclopentylidene; 1,1-cyclohexylidene; 3,3,5-trimethyl-1,1-cyclohexylidene; 3-methyl-1,1-cyclohexylidene; 2-[2.2.1]-bicycloheptylidene, neopentylidene, cyclopentadecylidene, cyclododecylidene, adamantylidene, and the like.

In one embodiment the dihydroxy aromatic compound represented by structure VII, E may be an unsaturated alkylidene group. Suitable dihydroxy-substituted aromatic hydrocarbons of this type include those of the formula IX:

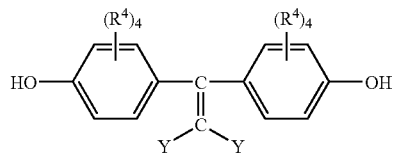

IX wherein independently each $R^4$ is independently at each occurrence hydrogen, chlorine, bromine, fluorine, or a $C_{1-20}$ monovalent aliphatic radical (for example a methyl group, a t-butyl group, or a methoxy group), and each Y is independently at each occurrence hydrogen, chlorine, bromine, or fluorine.

Suitable dihydroxy-substituted aromatic hydrocarbons also include those of the formula X:

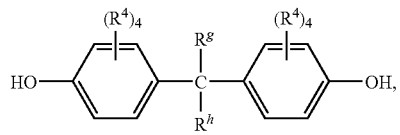

X wherein each $R^4$ is independently hydrogen, chlorine, bromine, fluorine, or a $C_{1-20}$ monovalent aliphatic radical (for example a methyl group, a t-butyl group, or a methoxy group), and $R^g$ and $R^h$ are independently hydrogen, a $C_1$-$C_{20}$ aliphatic radical, a $C_3$-$C_{20}$ cycloaliphatic radical, or a $C_4$-$C_{20}$ aromatic radical. Further $R^g$ and $R^h$ may together form a $C_4$-$C_{20}$ cycloaliphatic radical.

In some embodiments of the present invention, dihydroxy-substituted aromatic hydrocarbons that may be used comprise those disclosed by name or formula (generic or specific) in U.S. Pat. Nos. 2,991,273; 2,999,835; 3,028,365; 3,148,172; 3,153,008; 3,271,367; 3,271,368; and 4,217,438. In other embodiments of the invention, dihydroxy-substituted aromatic hydrocarbons comprise bis(4-hydroxyphenyl)sulfide; bis(4-hydroxyphenyl)ether; bis(4-hydroxyphenyl)sulfone; bis(4-hydroxyphenyl)sulfoxide; 1,4-dihydroxybenzene; 4,4'-oxydiphenol; 2,2-bis(4-hydroxyphenyl)hexafluoropropane; 4,4'-(3,3,5-trimethylcyclohexylidene)diphenol; 4,4'-bis(3,5-dimethyl)diphenol; 1,1-bis(4-hydroxy-3-methylphenyl)cyclohexane; 4,4-bis(4-hydroxyphenyl)heptane; 2,4'-dihydroxydiphenylmethane; bis(2-hydroxyphenyl)methane; bis(4-hydroxyphenyl)methane; bis(4-hydroxy-5-nitrophenyl)methane; bis(4-hydroxy-2,6-dimethyl-3-methoxyphenyl)methane; 1,1-bis(4-hydroxyphenyl)ethane; 1,2-bis(4-hydroxyphenyl)ethane; 1,1-bis(4-hydroxy-2-chlorophenyl) ethane; 2,2-bis(3-phenyl-4-hydroxyphenyl)propane; 2,2-bis(4-hydroxy-3-methylphenyl)propane; 2,2-bis(4-hydroxy-3-ethylphenyl)propane; 2,2-bis(4-hydroxy-3-isopropylphenyl) propane; 2,2-bis(4-hydroxy-3,5-dimethylphenyl)propane; 3,5,3',5'-tetrachloro-4,4'-dihydroxyphenyl)propane; bis(4-hydroxyphenyl)cyclohexylmethane; 2,2-bis(4-hydroxyphenyl)-1-phenylpropane; 2,4'-dihydroxyphenyl sulfone; 2,5-dihydroxy naphthalene; 2,6-dihydroxy naphthalene; hydroquinone; resorcinol; $C_{1-3}$ alkyl-substituted resorcinols; 4-methyl resorcinol; catechol; 1,4-dihydroxy-3-methylbenzene; 2,2-bis(4-hydroxyphenyl)butane; 2,2-bis(4-hydroxyphenyl)-2-methylbutane; 1,1-bis(4-hydroxyphenyl)cyclohexane; 4,4'-dihydroxydiphenyl; 2-(3-methyl-4-hydroxyphenyl)-2-(4-hydroxyphenyl)propane; 2-(3,5-dimethyl-4-hydroxyphenyl)-2-(4-hydroxyphenyl)propane; 2-(3-methyl-4-hydroxyphenyl)-2-(3,5-dimethyl-4-hydroxyphenyl)propane; bis(3,5-dimethylphenyl-4-hydroxyphenyl)methane; 1,1-bis(3,5-dimethylphenyl-4-hydroxyphenyl) ethane; 2,2-bis(3,5-dimethylphenyl-4-hydroxyphenyl) propane; 2,4-bis(3,5-dimethylphenyl-4-hydroxyphenyl)-2-methylbutane; 3,3-bis(3,5-dimethylphenyl-4-hydroxyphenyl)pentane; 1,1-bis(3,5-dimethylphenyl-4-hydroxyphenyl)cyclopentane; 1,1-bis(3,5-dimethylphenyl-4-hydroxyphenyl)cyclohexane; bis(3,5-dimethyl-4-hydroxyphenyl)sulfoxide; bis(3,5-dimethyl-4-hydroxyphenyl)sulfone; bis(3,5-dimethylphenyl-4-hydroxyphenyl)sulfide; and like bisphenols. In a particular embodiment the dihydroxy-substituted aromatic hydrocarbon is bisphenol A.

In some embodiments the dihydroxy-substituted aromatic compounds represented by structure VII includes compounds comprising one or more fused rings represented by component "E", attached to one or more aromatic groups $A^1$. Suitable dihydroxy-substituted aromatic hydrocarbons of this type include those containing indane structural units such as represented by the formula (XI), 3-(4-hydroxyphenyl)-1,1,3-trimethylindan-5-ol; and by the formula (XII), 1-(4-hydroxyphenyl)-1,3,3-trimethylindan-5-ol.

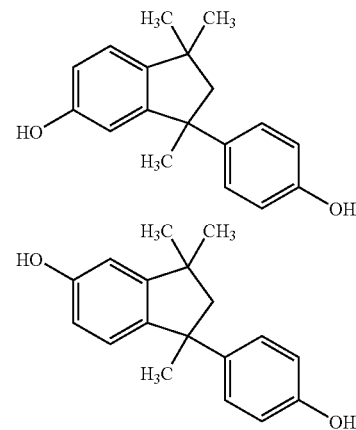

Also included with the class of dihydroxy aromatic compounds represented by formula VII are bisphenols comprising spirocyclic structures as component "E", for example as in 2,2,2',2'-tetrahydro-1,1'-spirobi[1H-indene]diol.

The term "alkyl" as used in the various embodiments of the present invention falls within the definition of an "aliphatic radical" as defined herein and includes both linear alkyl groups such as methyl groups, and branched alkyl groups such as isobutyl groups.

The salt of at least one aromatic hydroxy compound employed in the present invention is typically a sodium or potassium salt. Sodium salts are often used in particular embodiments by reason of their availability and relatively low cost. In one embodiment, the salt of at least one aromatic hydroxy compound is a disodium salt of a dihydroxy aromatic compound.

In one embodiment the salt of the aromatic hydroxy compound is generated in-situ, from an organic compound which is not itself an aromatic hydroxy compound. For example, the salt of hydroxyimide XIII may be formed in-situ from the corresponding chloroimide. For example, 4-chloro-N-methylphthalimide reacts with sodium hydroxide in a reaction mixture comprising a phosphazenium salt phase transfer catalyst to afford 4-hydroxy-N-methylphthalimide which is then deprotonated by sodium hydroxide, typically at a rate faster than its formation, to afford the corresponding sodium salt. Alternately, 4-chloro-N-methylphthalimide reacts with an oxygen nucleophile such as potassium carbonate or sodium acetate to afford an intermediate which subsequently converted to the salt of hydroxyimide XIII. In aromatic hydroxy compounds represented by

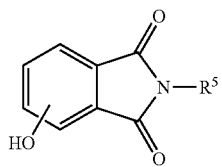

XIII structure XIII, $R^5$ is typically an organic radical selected from the group consisting of $C_1$-$C_{12}$ aliphatic radicals, $C_3$-$C_{12}$ cycloaliphatic radicals, and $C_4$-$C_{30}$ aromatic radicals. In an alternate embodiment, the aromatic hydroxy compound has the formula XIV.

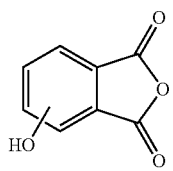

XIV

The reaction may be performed in the absence a solvent, or alternatively in the presence of a solvent. Preferably, the reaction is carried out in the presence of at least one inert solvent. Suitable solvents include non-polar solvents and polar aprotic solvents (also referred to as "dipolar aprotic solvents"). Typically, the reaction is carried out in an aromatic solvent, for example an aromatic hydrocarbon solvent or chloroaromatic solvent. In one embodiment the solvent has a boiling point above about 120° C., preferably above about 150° C., and more preferably above about 180° C. Suitable solvents include, but are not limited to, toluene, xylene, ortho-dichlorobenzene (o-DCB), para-dichlorobenzene, dichlorotoluene; 1,2,4-trichlorobenzene; diphenylether, dimethylsulfone, diphenyl sulfone, sulfolane, phenetole, anisole, veratrole, and mixtures thereof. In a preferred embodiment chlorinated aromatic liquids be employed as solvents, examples of which include, but are not limited to, ortho-dichlorobenzene (o-DCB); 2,4-dichlorotoluene; and 1,2,4-trichlorobenzene. In some embodiments 2,4-dichlorotoluene is a preferred solvent. In the case of some solvents, such as ortho-dichlorobenzene, the proportion of phase transfer catalyst can be increased and/or the reaction can be run at super-atmospheric pressure to permit higher temperatures and higher reaction rates.

Typically, the aromatic compound comprising at least one leaving group is a compound having formula XV, wherein $Ar^1$ is independently at each occurrence a $C_3$-$C_{20}$ aromatic radical, $L^1$ is a leaving group independently selected from the group consisting of fluoro, chloro, bromo, iodo, nitro, and organosulfonate groups; B is an activating group, and g is 1, 2 or 3. Organosulfonate groups are illustrated by the methanesulfonate (MeSO$_3$—), tosylate (C$_7$H$_7$SO$_3$—), and trifluoromethanesulfonate (CF$_3$SO$_3$—) groups.

XV

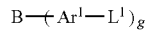

In one embodiment the aromatic radical $Ar^1$ is a monocyclic aromatic radical, for example a phenylene (C$_4$H$_4$) radical, $L^1$ is a chlorine atom, B is a sulfonyl group, and g is 2. The activating group B, is typically an electron-withdrawing group, which may be monovalent or polyvalent group. The activating group B is illustrated by halo, nitro, acyl, cyano, carboxy, carbonyl, alkoxycarbonyl, aldehydo, sulfonyl, and perfluoroalkyl. In addition B may be a heterocyclic aromatic activating group such as pyridyl. Examples of divalent groups which may serve as component "B" in structure XV include the carbonyl group, carbonylbis(arylene) groups, sulfonyl groups, bis(arylene) sulfone groups, benzo-1,2-diazine groups, and azoxy groups. When "g" in structure XV is 2, the moiety "—Ar$^1$—B—Ar$^1$—" is illustrated by a bis(arylene) sulfone moiety, a bis(arylene)ketone moiety, a bis(arylene) benzo-1,2-diazine moiety, and a bis(arylene)azoxy moiety.

Compounds represented by structure XV include compounds wherein component "B" together with Ar$^1$, form a fused ring system such as benzimidazole, benzoxazole, quinoxaline or benzofuran. In such compounds, L$^1$ includes leaving groups such as fluoro, chloro, bromo, iodo, nitro groups. Fluoro and chloro groups are frequently preferred.

In one embodiment, the aromatic compound comprising at least one leaving group is a is a bisimide having structure XVI

XVI

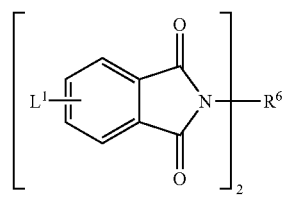

wherein L$^1$ is defined as in structure XV, and R$^6$ is selected from the group consisting of divalent C$_1$-C$_{12}$ aliphatic radicals, divalent C$_3$-C$_{12}$ cycloaliphatic radicals, and divalent C$_4$-C$_{30}$ aromatic radicals.

In a further embodiment R$^6$ is a divalent aromatic radical having structure XVII

XVII

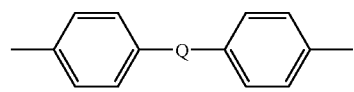

wherein Q is a C$_1$-C$_{12}$ aliphatic radical, a C$_3$-C$_{12}$ cycloaliphatic radical, a C$_4$-C$_{18}$ aromatic radical, an oxygen, atom, a sulfur atom, a sulfinyl group, a sulfonyl group, a selenium atom or a bond. In a preferred embodiment R$^6$ is selected from the group consisting of m-phenylene, p-phenylene, 4,4'-oxybis(phenylene).

In an alternate embodiment the aromatic compound comprising at least one leaving group is selected from the group consisting of compounds having formula XVIII

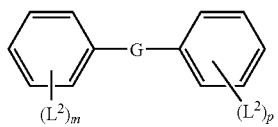

XVIII wherein G is a carbonyl group (—CO—), or a sulfonyl group (—SO$_2$—); L$^2$ is independently at each occurrence a fluoro, chloro, bromo, iodo, nitro, or a trifluormethansulfonate group; and "m" and "p" are independently integers from 0-5, wherein not both m and p are zero.

In one embodiment the aromatic compound comprising at least one leaving group is selected from the group consisting of bis(4-fluorophenyl)sulfone, bis(4-chlorophenyl)sulfone, bis(4-fluorophenyl)ketone, and bis(4-chlorophenyl)ketone.

In an alternate embodiment the aromatic compound comprising at least one leaving group is selected from the group consisting of 1,3- and 1,4-bis[N-(4-fluorophthalimido)]benzene and 4,4'-bis[N-(4-fluorophthalimido)]phenyl ether and the corresponding chloro, bromo and nitro compounds.

In yet another embodiment the aromatic compound comprising at least one leaving group is selected from the group of substituted aromatic imides having structure XIX

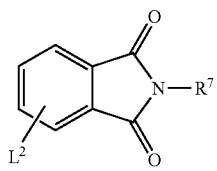

XIX wherein R$^7$ is selected from the group consisting of monovalent C$_1$-C$_{12}$ aliphatic radicals, monovalent C$_3$-C$_{12}$ cycloaliphatic radicals, and monovalent C$_4$-C$_{30}$ aromatic radicals; and L$^2$ is a fluoro, chloro, bromo, iodo, or nitro group. Suitable substituted aromatic imides include 3-choro-N-methylphthalimide, 4-choro-N-methylphthalimide, 3-fluoro-N-butylphthalimide, 4-fluoro-N-butylphthalimide, 3-choro-N-cyclohexylphthalimide, 4-choro-N-cyclohexylphthalimide, 3-chloro-N-phenylphthalimide, 4-chloro-N-phenylphthalimide, and the like.

In yet another embodiment the aromatic compound comprising at least one leaving group is selected from the group of substituted phthalic anhydrides XX

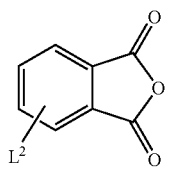

XX wherein L$^2$ is a fluoro, chloro, bromo, iodo, or nitro group. Suitable substituted phthalic anhydrides include, 3-chlorophthalic anhydride, 4-chlorophalic anhydride, 3-fluorophthalic anhydride, and the like.

In yet still another embodiment, the aromatic compound comprising at least one leaving group is selected from the group of compounds represented by structures XXI and XXII

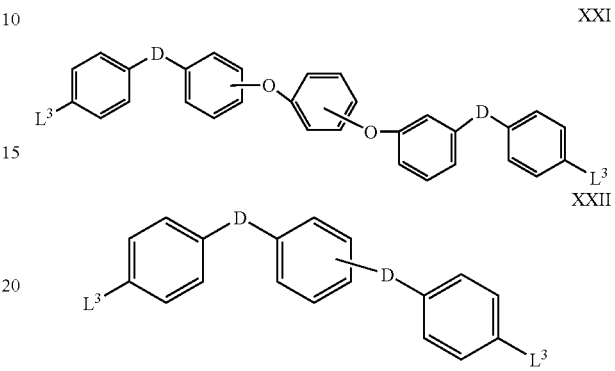

wherein D is independently at each occurrence a carbonyl group or a sulfonyl group, and L$^3$ is independently at each occurrence a fluoro, chloro, bromo, iodo, or nitro group. Compounds XXI are illustrated by the PEEK monomers 1,1'-(p-phenylenedioxy)bis[4-(4-chlorobenzoyl)]benzene; 1,1'-(p-phenylenedioxy)bis[4-(4-fluorobenzoyl)]benzene, and the like. Compounds XXII are illustrated by 1,3-bis(4-chlorobenzoyl)benzene; 1,3-bis(4-fluorobenzoyl)benzene; 1,4-bis(4-chlorobenzoyl)benzene; 1,3-bis(4-chlorophenylsulfonyl)benzene; and the like.

When the reaction between the salt of at least one aromatic hydroxy compound and at least one aromatic compound comprising at least one leaving group is complete, the product aromatic ether may be isolated by conventional techniques. It is often convenient to filter the product mixture while still hot to remove insoluble by-products, and subsequently cool the filtrate, whereupon the desired aromatic ether precipitates and may be collected by filtration.

In one embodiment the contacting in a reaction mixture the salt of at least one aromatic hydroxy compound with at least one aromatic compound comprising at least one leaving group is carried out at a temperature in a range from about 50° C. to about 250° C., preferably from about 120° C. to about 250° C., and still more preferably from about 150° C. to about 250° C. In an alternate embodiment the contacting is carried out at a temperature range from about 150° C. to about 225° C. Typically, the contacting is carried out at atmospheric pressure under inert atmosphere, for example under a nitrogen atmosphere.

EXAMPLES

The following examples are set forth to provide those of ordinary skill in the art with a detailed description of how the methods claimed herein are evaluated, and are not intended to limit the scope of what the inventors regard as their invention. Unless indicated otherwise, parts are by weight, and temperature is in ° C.

Yields in the reactions of 4-chlorophenyl phenyl sulfone were determined using an internal standard HPLC method. These reactions are at times referred to as "model" reactions since they often predict (or model) the behavior of more complex polymerization reactions. Phenanthrene was used as the internal standard in all cases, and was added to the reactions along with the reactants. Aliquots of the reaction mixture were removed periodically during the reaction, and quenched with 2 drops of acetic acid. The quenched aliquots were diluted with 2 milliliters of tetrahydrofuran (hereinafter known as "THF"), filtered, and analyzed on a Zorbax 150 cm×4.6 mm C-8 column, eluting with a THF-water gradient. Recovered bisphenol A, solvent, phenanthrene, starting substrate, and product bis-sulfone were separated, and the amount of starting material and product could be quantified by comparing to the internal standard. The HPLC was calibrated by using pure isolated bis-sulfone product relative to phenanthrene. No mono-substitution product was noted in any case.

Gel permeation chromatography (hereinafter known as GPC) characterization was carried out using Turbogel® Software on a commercial GPC system using a Polymer Labs Mixed C column, at a column temperature of 40° C., eluting with 3% isopropanol/chloroform at 0.7 milliliter per minute, using an Agilent HPLC pump and UV detection at 255 nm. The system was calibrated with polystyrene standards daily, using a third order fit. The correlation coefficient was typically about 0.9996. Sample size was 5-10 microliters. Two to three drops of polymer solution were added to 2 drops acetic acid in approximately 0.25 mL o-dichlorobenzene, to quench the polymerization reaction. The sample was diluted with 1 milliliter of chloroform, rinsing the pipette with sufficient chloroform to ensure that all of the product polymer was dissolved. Water (1 milliliter) was added with stirring to dissolve the by-product sodium chloride. Ten drops of the lower (chloroform) phase were added to a sample filter, diluted with 1 milliliter of chloroform and filtered through a 0.45 micron polytetrafluoroethylene membrane. The contents were placed directly into a sampling vial, and analyzed by GPC. Molecular weights are reported as number average ($M_n$) or weight average ($M_w$) molecular weight.

Preparation of Phosphazenium Salt

A phosphazene base, P 2-Ethyl[1-ethyl-2,2,4,4,4-pentakis (dimethylamino)-2$\lambda$5,4$\lambda$5-catenadi(phosphazene)] (CAS No.:165535-45-5, Aldrich Chemical Co., 679 mg; 2.0 millimoles) was dissolved in 5 milliliters of chloroform and cooled to 0° C. About 2.0 mmol of methyl methanesulfonate (178 µL) was added to the above solution while maintaining the temperature at 0° C. The proton NMR was recorded at the end of one hour of reaction, and indicated that all of the methylsulfonate had reacted. The solvent was removed by rotary evaporation and o-dichlorobenzene (o-DCB) was added. The resulting solution was heated and a small amount of o-DCB was distilled in order to dry the solution of the phosphazenium salt. The concentration of the phosphazenium salt was determined by proton NMR.

General Procedure for Model Reactions (Displacement Reactions of 4-chlorophenyl Phenyl Sulfone)

Dry bisphenol A disodium salt ($BPANa_2$) was weighed into a 50-mL flask, and a 2 mole % excess of 4-chlorophenyl phenyl sulfone was added. The transfers were carried out in a dry box. The flask was capped, removed from the dry box, and was fitted with a condenser and a nitrogen purge. Sufficient solvent was added to achieve a final product concentration to approximately 20 weight %, assuming quantitative conversion of starting materials to product. Phenanthrene was added (typically 100 mg) as an internal standard. The reaction mixture was stirred magnetically while being heated to reflux. Once reflux had been achieved, the phase transfer catalyst (PTC) was added, and the timer was started. Samples were removed periodically, and were analyzed by HPLC.

Figure 2:
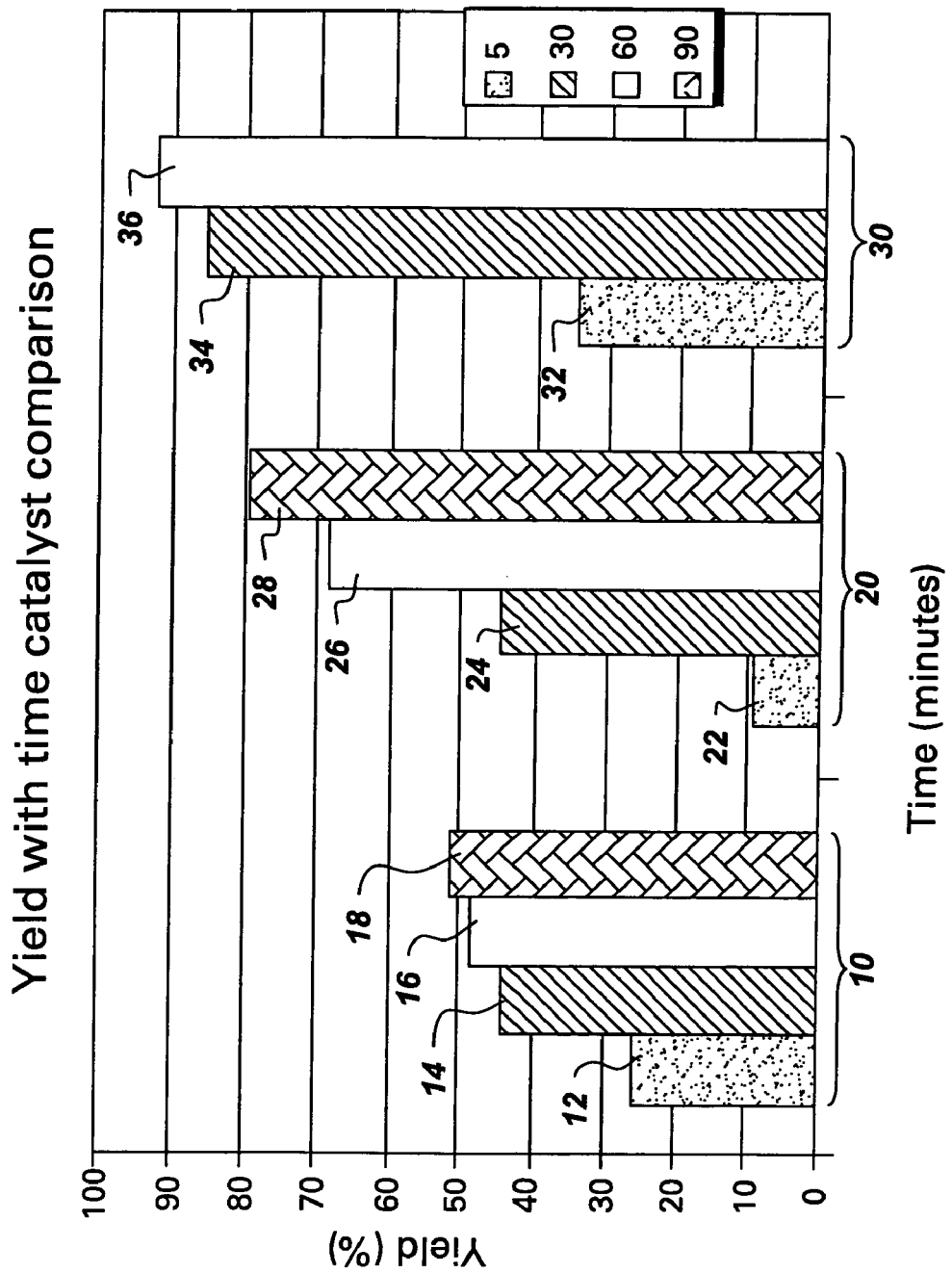
FIG. 2 compares the reaction kinetics observed in a series of reactions involving the 4-chlorophenyl phenyl sulfone and the disodium salt of bisphenol A in the presence of either a guanidinium salt phase transfer catalyst, or a phosphazenium salt phase transfer catalyst.

FIGS. 1 and 2 illustrate the behavior of the new phase transfer catalysts in the formation of 1,1'-(1-methylethylidene)bis[4-[4-(phenylsulfonyl)phenoxy]benzene (CAS No. 90139-53-0). When the P2-EthylMethyl mesylate was used as a PTC at 1.0 mole % in the model reaction in refluxing o-DCB at 180° C. (See 4 (FIG. 1)), the reaction exhibited pseudo-first order kinetics. This indicates that no catalyst decomposition nor diminution in rate was occurring during the reaction. In order to further test the stability of the phosphazenium salt, similar reactions were carried out at higher temperatures, in 3,4-dichlorotoluene (bp=200° C.) (See 6 (FIG. 1)) and in 1,2,4-trichlorobenzene (bp=214° C.) (See 2 (FIG. 1)). As shown in FIG. 1, even at 200° C., essentially linear reaction kinetics were observed, indicating no decomposition of the P2-EthylMethyl mesylate phase transfer catalyst. In trichlorobenzene, only a small amount of decomposition was observed, after 60 minutes (See 2 (FIG. 1)). In this instance only 0.5 mole % catalyst was used, since after initial range-finding experiments it was determined that reaction using 1.0 mole % would be too fast to follow accurately at 214° C.

The results shown in FIG. 1 illustrate that because they are highly stable, the phosphazenium salt phase transfer catalysts are effective over a broad range of temperatures. Under the reaction conditions examined (2, 4, 6 FIG. 1) the stability of the phosphazenium salt catalyst was observed to be superior relative to a representative guanidinium salt phase transfer catalyst, hexaethylguanidium chloride (HEGCl). FIG. 2 illustrates the enhanced stability of the phosphazenium catalysts and compares a reaction utilizing HEGCl in o-DCB at 180° C. (See 10 FIG. 2) to the same reaction using a phosphazenium catalyst at either 180° C. (See 20 FIG. 2) or at 200° C. (See 30 FIG. 2). Although HEGCl provides a faster initial rate (See 12 FIG. 2) than the phosphazenium salt at 180° C. (See 22 FIG. 2), the reactions incorporating a phosphazenium salt phase transfer catalyst ultimately give higher yields (Compare 18, 28, and 36 FIG. 2). At 200° C. (30, FIG. 2), the rate increase obtained by increasing the reaction temperature more than compensates for the relative effectiveness of the catalysts, and reaction rates faster than could be achieved with HEGCl were obtained (Compare 12 and 32 FIG. 2).

General Procedure for PTC Mediated Polymerization

An accurately weighed amount (typical lab-scale amounts were approximately 10 grams) of bisphenol A disodium salt (abbreviated here as $BPANa_2$) was transferred in a dry box into an oven-dried, 250-mL, 3-necked flask. (An electronic balance, capable of 0.1 mg accuracy was used in the dry box). The flask was capped and transferred to an oil bath maintained at 205° C., at which point it was fitted with a nitrogen sparge tube atop a reflux condenser, a mechanical stirrer, and a distillation apparatus. The required amount of solvent to provide a solution of 30 wt % polymer in solvent, plus an additional 20 mL was added to the flask. The solvent was distilled at atmospheric pressure, while checking the distillate by Karl-Fischer titration to ensure dryness. If Karl-Fischer titration of the distillate indicated the salt was dry after the 20 mL solvent had distilled, then the required amount of 4,4'-dichlorodiphenylsulfone was added, along with an additional 10 mL of solvent. Again, the excess solvent was distilled, affording a slurry of reactants in dry solvent. At this stage there was no evidence that any displacement reaction had occurred. Upon the addition of the catalyst in dry o-DCB solution, the displacement reaction initiated, and timing was begun. Samples were removed periodically and analyzed by GPC analysis. When the desired weight average molecular weight ($M_w$) was met, the reaction was quenched by the addition of approximately 0.5 mL of phosphoric acid.

Figure 3:
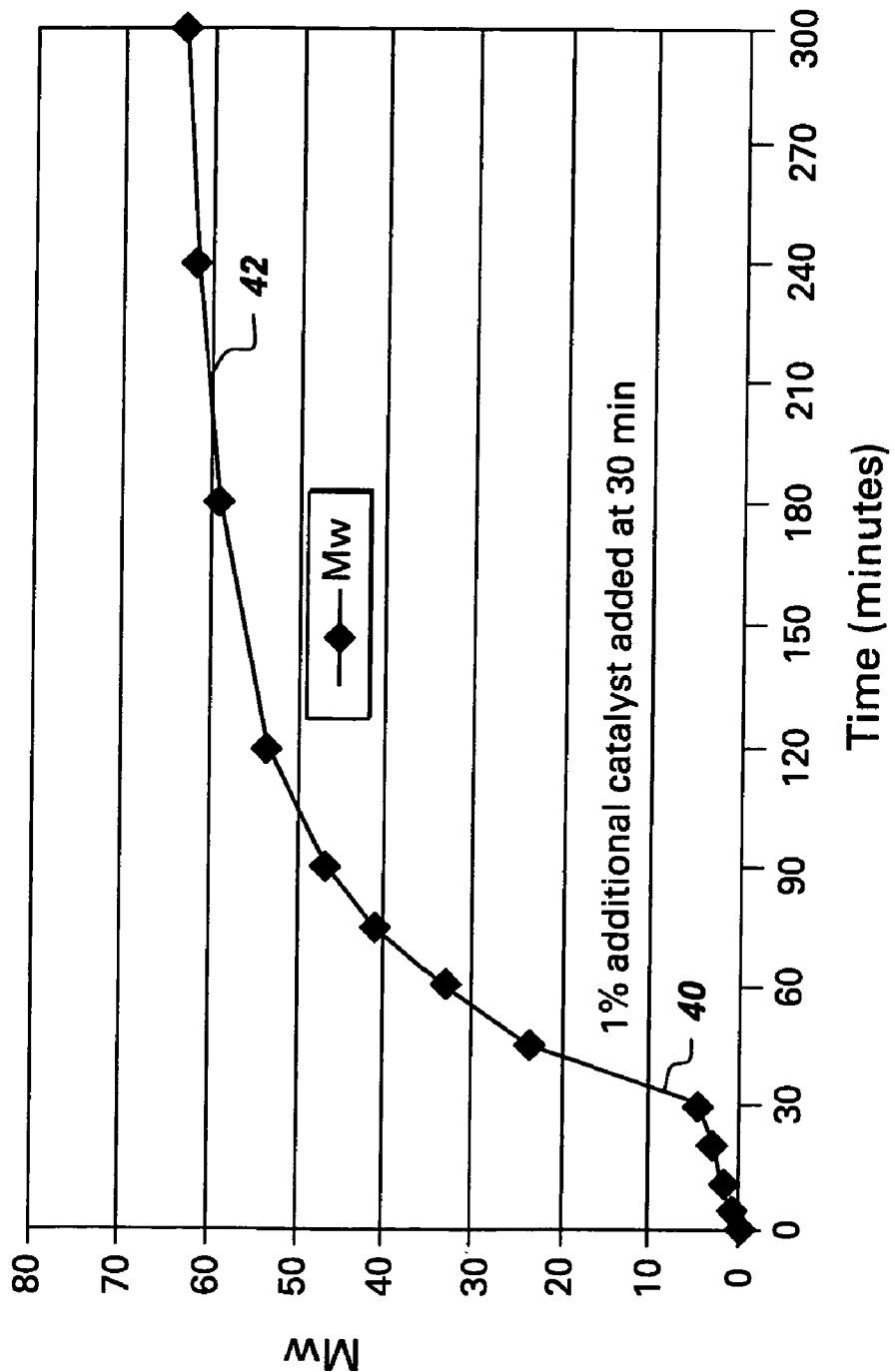
FIG. 3 illustrates the rate of polymerization observed in a reaction between bis(4-chlorophenyl)sulfone and the disodium salt of bisphenol A in the presence of 2 mole percent phosphazenium salt phase transfer catalyst at 180° C.
Figure 4:
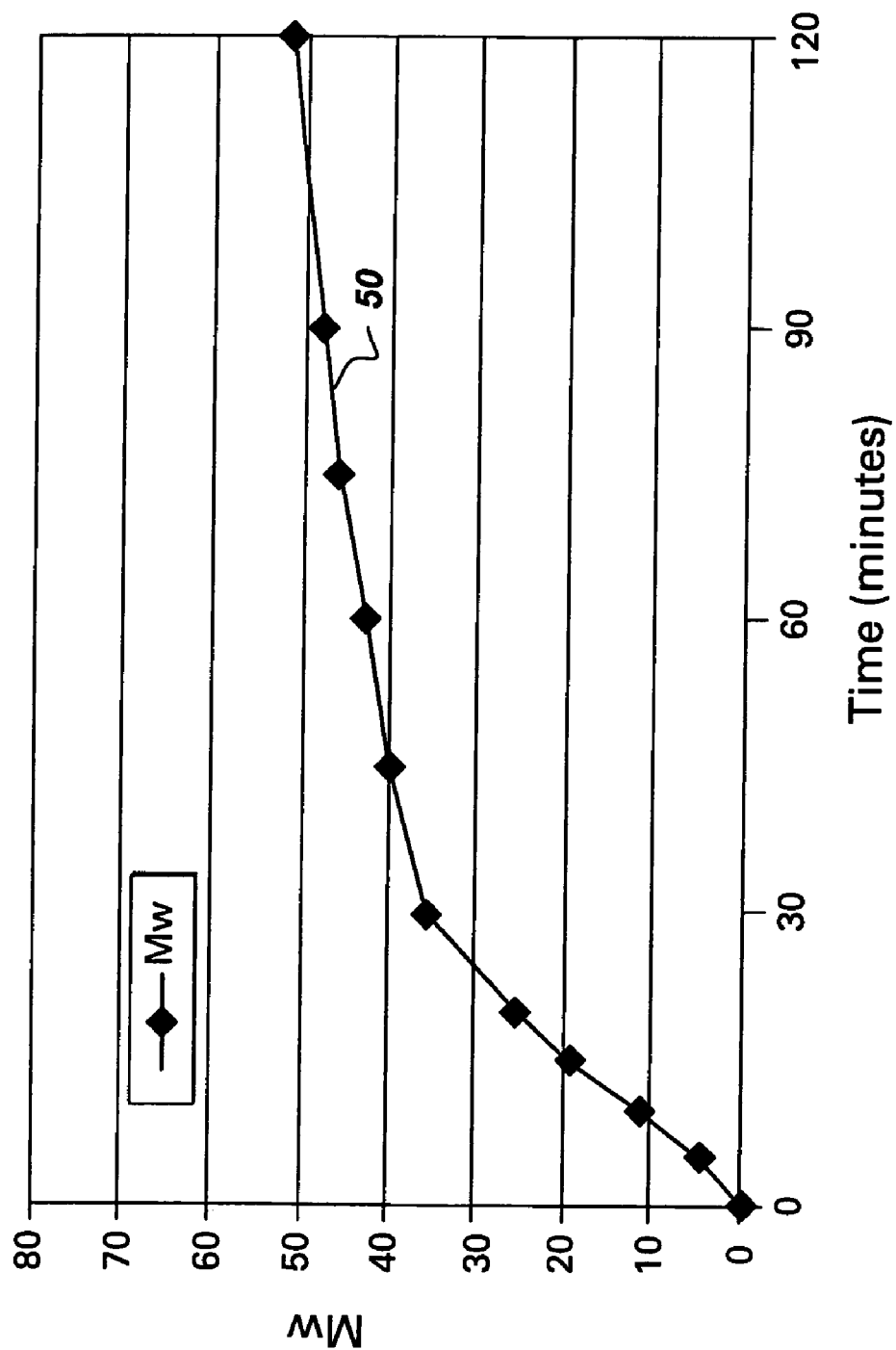
FIG. 4 illustrates the rate of polymerization observed in a reaction between bis(4-chlorophenyl)sulfone and the disodium salt of bisphenol A in the presence of 1 mole percent phosphazenium salt phase transfer catalyst at 200° C.

FIGS. 3 and 4 illustrate the effectiveness of the phosphazenium catalyst in polymerization reactions (See 42 FIGS. 3 and 50 FIG. 4). The efficiency of catalysis is readily apparent. In FIG. 3, the reaction was run in o-DCB at 180° C. using 1 mole percent of the phosphazenium catalyst. After 30 minutes at 180° C. an additional 1 mole percent of the phosphazenium catalyst was added. The additional catalyst resulted in the significant rate enhancement observed at 40 (FIG. 3) and the molecular weight of the growing polymer chain was greater than 40,000 daltons in less than 90 minutes.

FIG. 4 illustrates the same reaction in a higher boiling solvent, dichlorotoluene, at 200° C. In the reaction only 1 mole % phosphazenium catalyst was employed. The molecular weight of the growing polymer chain in the reaction illustrated in FIG. 4 was greater than 40,000 daltons in less than 60 minutes.

Further evidence that the phosphazenium salt phase transfer catalysts of the present invention show enhanced stability and effectiveness relative to guanidinium catalysts (e.g. HEGCl) is illustrated by the following examples. Whereas polymerization of an 80/20 biphenol/BPA mixture required 500-700 minutes to reach Mw approximately 50,000 using 2.0 mole % HEGCl in refluxing o-DCB, similar reaction using $BPANa_2$ reached 54,000 in just 120 minutes. Reducing the phosphazenium catalyst level to 1.0% and increasing the reaction temperature to 200° C. by carrying out the reaction in refluxing dichlorotoluene also gave excellent results: The polymer reached Mw=51,650 daltons in just 2 hours. Similar reaction using 1% HEGCl in o-DCB required more than 40 hours to reach that Mw. Thus, it has been found that because of the enhanced stability of the phosphazenium catalysts of the present invention, the rates of chemical reactions employing said catalysts can be increased merely by increasing the reaction temperature without destroying the catalyst. Further, the enhanced stability of the phosphazenium catalysts of the present invention provides for a reduction in the amount of catalyst need in reactions employing phase transfer catalysts.

The invention has been described in detail with particular reference to preferred embodiments thereof, but it will be understood by those skilled in the art that variations and modifications can be effected within the spirit and scope of the invention.

What is claimed is:

1. A method for making an aromatic polyether sulfone, said method comprising contacting in a reaction mixture the disodium salt of bisphenol A with bis(4-chlorophenyl)sulfone, said contacting being carried out in the presence of a phosphazenium salt having structure I

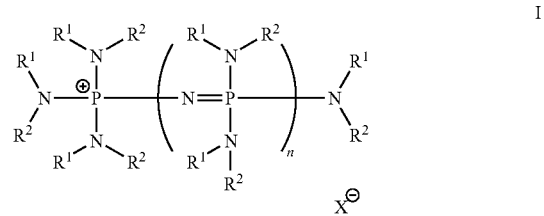

wherein n is an integer from zero to about 10, $R^1$ and $R^2$ are independently selected from the group consisting of $C_1$-$C_{20}$ aliphatic radicals, $C_3$-$C_{20}$ cycloaliphatic radicals, and $C_4$-$C_{20}$ aromatic radicals, and wherein said $R^1$ and $R^2$ may be linked together form a cyclic structure comprising at least one nitrogen atom, and wherein X is selected from the group consisting of monovalent inorganic anions, monovalent organic anions, polyvalent inorganic anions, polyvalent organic anions, and mixtures thereof, said contacting being carried out at a temperature in a range between about 200° C. and about 250° C., said contacting being carried out in the presence of orthodichlorobenzene.

\* \* \* \* \*